United States Patent

Uchida et al.

Patent Number: 5,886,205
Date of Patent: Mar. 23, 1999

[54] PROCESS FOR PRODUCING SILICON-CONTAINING ISOCYANATE COMPOUND

[75] Inventors: Takashi Uchida; Hiroya Okumura, both of Fujisawa; Takashi Shibata, Kamakura; Masaaki Sasaki, Kashima, all of Japan

[73] Assignee: Takeda Chemical Industries, Ltd., Osaka, Japan

[21] Appl. No.: 843,638

[22] Filed: Apr. 10, 1997

[30] Foreign Application Priority Data

Apr. 15, 1996 [JP] Japan .................................. 8-092660
Mar. 12, 1997 [JP] Japan .................................. 9-057709

[51] Int. Cl.⁶ ...................................................... C07F 7/10
[52] U.S. Cl. ........................................................... 556/414
[58] Field of Search .............................................. 556/414

[56] References Cited

U.S. PATENT DOCUMENTS

| | | | |
|---|---|---|---|
| 3,598,852 | 8/1971 | Berger | 556/414 |
| 3,607,901 | 9/1971 | Berger | 260/448.2 |
| 4,064,151 | 12/1977 | Hedaya et al. | 556/414 |
| 5,393,910 | 2/1995 | Mui et al. | 556/414 |

FOREIGN PATENT DOCUMENTS

| | | |
|---|---|---|
| 5-8713 | 2/1993 | Japan . |
| 6-228161 | 8/1994 | Japan . |
| 7-258273 | 10/1995 | Japan . |

*Primary Examiner*—Paul F. Shaver
*Attorney, Agent, or Firm*—Wenderoth, Lind & Ponack, L.L.P.

[57] ABSTRACT

A process for producing silicon-containing isocyanate compounds of the general formula II, comprising thermally induced decomposition of a silicon-containing carbamic ester of the general formula I at a pH of not higher than 8 in the presence of a catalyst of at least one metal or its compound.

General Formula I:

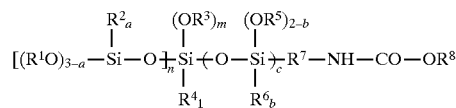

General Formula II:

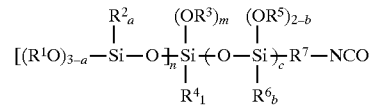

wherein $R^1$ to $R^6$ and $R^8$ each represent a hydrocarbon group, $R^7$ represents an alkylene group having 1 to 8 carbon atoms, n, m and l represent an integer of 0 to 3 and m+n+l=3, and a, b and c represent integers of 0 to 3, 0 to 2, and 0 to 8, respectively.

5 Claims, No Drawings

PROCESS FOR PRODUCING SILICON-CONTAINING ISOCYANATE COMPOUND

BACKGROUND OF THE INVENTION

1. Field of the Invention

The present invention relates to a process for producing silicon-containing isocyanate compounds by the thermally induced decomposition of urethane compounds which are carbamic esters containing silicon and at least one alkoxysilyl group or one siloxane unit.

2. Description of the Related Art

An isocyanate group has a high reactivity and reacts with an organic functional group having an active hydrogen such as a hydroxyl group, a primary or secondary amino group or a carboxylic acid group to form a urethane bond or a urea bond. Therefore, an organic polysiloxane having an isocyanate group introduced into the organic compounds is useful as a silicone modifier for organic compounds having an active hydrogen. Processes for efficiently producing the polysiloxanes containing an isocyanate group were proposed (see Japanese Patent Laid-Open No. 6-228161 (1994)).

On the other hand, an alkoxysilyl group is also highly active, and polysiloxanes having such a functional group are useful as the silicone modifier. Further, it is known to use these polysiloxanes as a moisture curing agent, etc. Therefore, a silicon compound having an isocyanate group and at least one alkoxysilyl group in the organic compounds is highly valuable in the alkoxysilane modification of an active hydrogen-containing organic compound.

The isocyanate compounds are usually produced by phosgenation on an industrial scale. However, when a polysiloxane containing an amino group is reacted with phosgene, the intended polysiloxane-containing isocyanate compound cannot be obtained, since the siloxane bond is decomposed by hydrochloric acid formed as a by-product in the prior art. Also, when an alkoxysilylalkylamine having an alkoxysilicon bond is reacted with phosgene, the bond between the alkoxy and silicon is decomposed by hydrochloric acid formed as a by-product. Additionally, an alcohol thus formed reacts with the isocyanate to lower the yield of the intended alkoxysilyl group-containing isocyanate compound, drastically. On the other hand, Japanese Patent Publication No. 5-8713 (1993) discloses a process wherein the reaction of alkoxysilylalkylamine with phosgene is carried out in the presence of a tertiary amine to neutralize hydrochloric acid formed as a by-product.

However, this phosgenation process has problems both in handling highly toxic phosgene and in the treatment of hydrochloric acid, which is formed as a by-product in the process and easily corrodes the apparatus. Under these circumstances, investigations were made for the purpose of developing an industrial process to be employed in place of the above-described process. For example, a process wherein a carbamatoorganosilane is gasified and then this compound is decomposed by heating in a gas phase is disclosed in Japanese Patent Laid-Open No. 7-258273 (1995). However, undesirable decomposition of this compound per se might occur in addition to the intended thermally induced decomposition, or side reactions such as the polymerization of the formed isocyanate might occur, since a considerably high heat is applied to the carbamatoorganosilane for the gasification thereof.

U.S. Pat. No. 3,607,901 discloses a process for producing silicon-containing isocyanate compounds. Although γ-isocyanatopropyltrimethoxysilane is obtained by the thermally induced decomposition in Example 2 given in the specification, the yield of this product is only as low as 72.9%. It is pointed out that this process has another problem that since cyclic silyl carbamate formed as a by-product has a boiling point close to that of the intended product, the purification of the product is quite difficult.

Although various processes for producing isocyanate compounds containing silicon and an alkoxysilyl group were proposed as described above, these processes are those using highly toxic phosgene or vapor phase processes easily allowing undesirable side reactions in the gasification of the starting material. Thus, these known processes cannot provide the intended product with a high purity in a high yield and usually has economical advantages.

SUMMARY OF THE INVENTION

The object of the present invention is to provide a process for efficiently producing a highly pure silicon-containing isocyanate compound in a high yield from a urethane compound which is a carbamic ester.

After intensive investigations, the inventors have found a process for efficiently producing a highly pure isocyanate compound in a high yield by a thermally induced decomposition of a specified urethane compound, which is a carbamic ester, in the presence of at least one metal or metal compound in a reaction medium kept at a specified pH. The present invention has been completed on the basis of this finding.

Namely, the present invention provides a process for producing silicon-containing isocyanate compounds of the general formula II:

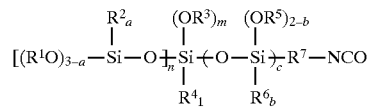

wherein $R^1$ to $R^6$ each represent a hydrocarbon group, $R^7$ represents an alkylene group having 1 to 8 carbon atoms, n, m and l represent an integer of 0 to 3 and m+n+l=3, a represents an integer of 0 to 3, b represents an integer of 0 to 2, and c represents an integer of 0 to 8, the process comprising thermally induced decomposition of a silicon-containing carbamic ester of the general formula I:

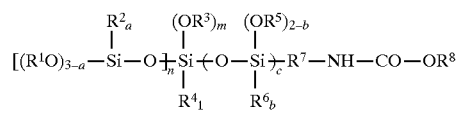

wherein $R^1$ to $R^7$, n, m, l, a, b and c are as defined above, and $R^8$ represents a hydrocarbon group, at a pH of not higher than 8 in the presence of a decomposition catalyst comprising at least one metal element or at least one metal compound.

DESCRIPTION OF THE PREFERRED EMBODIMENTS

The hydrocarbon groups $R^1$ to $R^6$ and $R^8$ in the above general formula I used in the present invention include, for example, alkyl groups having 1 to 9 carbon atoms, aryl groups having 6 to 20 carbon atoms and alkenyl groups having 2 to 10 carbon atoms. $R^7$ represents an alkylene group having 1 to 8 carbon atoms, which may be either linear or branched.

Examples of these compounds include methyl N-(α-trimethylsilylmethyl)carbamate, ethyl N-(α-triethylsilylmethyl)carbamate, methyl N-(α-trimethoxysilylmethyl)carbamate, methyl N-(α-dimethoxymethylsilylmethyl)carbamate, methyl N-(α-methoxydimethylsilylmethyl)carbamate, ethyl N-(α-triethoxysilylmethyl)carbamate, ethyl N-(α-diethoxyethylsilylmethyl)carbamate, methyl N-(γ-trimethylsilylpropyl)carbamate, ethyl N-(γ-triethylsilylpropyl)carbamate, methyl N-(γ-trimethoxysilylpropyl)carbamate, methyl N-(γ-dimethoxymethylsilylpropyl)carbamate, methyl N-(γ-methoxydimethylsilylpropyl)carbamate, ethyl N-(γ-triethoxysilylpropyl)carbamate, ethyl N-(γ-diethoxyethylsilylpropyl)carbamate, ethyl N-(γ-ethoxydiethylsilylpropyl)carbamate, ethyl N-(6-trimethoxysilylhexyl)carbamate, methyl N-(6-dimethoxymethylsilylhexyl)carbamate, ethyl N-(6-triethoxysilylhexyl)carbamate, ethyl N-(6-diethoxyethylsilylhexyl)carbamate, methyl N-[γ-tris(trimethoxysiloxy)silylpropyl]carbamate, methyl N-(γ-trimethoxysiloxydimethylsilylpropyl)carbamate, methyl N-(γ-trimethylsiloxydimethoxysilylpropyl)carbamate, ethyl N-[γ-tris(triethoxysiloxy)silylpropyl]carbamate, ethyl N-(γ-triethoxysiloxydiethylpropyl)carbamate, ethyl N-(γ-triethoxysiloxydiethoxysilylpropyl)carbamate, methyl N-[γ-tris(trimethylsiloxy)silylpropyl]carbamate and ethyl N-[6-tris(triethoxysiloxy)silylhexyl]carbamate.

Further, there may be mentioned compounds in which the repeated unit represented by general formula III in the foregoing general formula I is a linear organopolysiloxane represented by the formula IV.

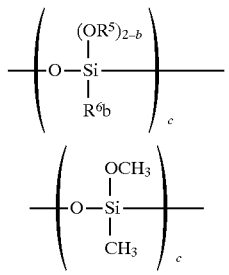

wherein b and c are integers of 0 to 2 and 0 to 8, respectively, as previously defined.

Examples having aryl group or groups as the hydrocarbon groups $R^1$ through $R^6$ and $R^8$ of the general formula I include compounds having phenyl group(s), naphthyl group(s), etc., in place of one or more alkyl groups of the compounds listed above. As examples having alkenyl groups as the hydrocarbon groups $R^1$ through $R^6$ and $R^8$ of the general formula I, there may be mentioned compounds having vinyl group(s), propenyl group(s), etc. in place of one or more alkyl groups of the compounds listed above. The carbamic esters of the general formula I may be compounds containing two or more different alkoxy groups in one molecule. The process for synthesizing the carbamic esters of the general formula I is not particularly limited. They can be produced by, for example, reacting a silyl group-containing alkylamine or alkoxysilyl group-containing alkylamine with a dialkyl carbonate in the presence of an alkali catalyst.

The metallic catalyst usable in the present invention is at least one metal element selected from the group consisting of Sn, Sb, Fe, Co, Ni, Cu, Cr, Ti, Pb, etc., or at least one metal compound thereof, such as oxide, halide, carboxylate, phosphate or organometallic compound and these catalysts are also used in the urethanation. Among them, Fe, Sn, Co and Sb are particularly preferred in the present invention, since they are highly effective and also they do not have a catalytic effect on the by-product formation. In particular, the metallic catalyst of Fe or Sn are still preferred, since the reaction rapidly proceeds to form the isocyanate compound of the general formula II in a short time in the presence thereof. The Sn compounds include, for example, tin oxides, tin chlorides, tin bromides, tin iodides, tin formates, tin acetates, tin oxalates, tin stearates, tin oleates, tin phosphates, dibutyltin dichlorides, dibutyltin dilaurates and 1,1,3,3-tetrabutyl-1,3-dilauryloxydistanoxane. The Fe compounds include, for example, iron acetates, iron benzoates, iron naphthenates and iron acetylacetonates. The catalyst is used in an amount in the range of 0.0001 to 5% by weight (in terms of metal element or its compound), preferably 0.01 to 1% by weight, based on the reaction solution.

The solvent used in the present invention must be the one which is inert to the carbamic ester compound of the general formula I and also to the produced isocyanate compound of the general formula II and have a boiling point higher than that of the produced isocyanate compound. It is preferred to use the inert solvent, since when it is not used, the concentration of the carbamic ester is high and side reactions such as the polymerization of the alkoxysilyl group are caused in the course of the reaction carried out for a long time and make it difficult to obtain the intended isocyanate compound in a high yield. The solvents are, for example, dioctyl phthalate, didecyl phthalate, didodectyl phthalate or other similar esters, dibenzyltoluene, triphenylmethane, phenylnaphthalene, biphenyl, diethylbiphenyl and triethylbiphenyl, usually used as a heat transfer medium. The inert solvent is used in a weight proportion in the range of 0 to 100 parts, preferably 0.01 to 50 parts and more preferably 0.1 to 20 parts, per part of the starting carbamic ester of the general formula I.

The pH in the reaction is controlled at 8 or below, preferably 4 to 8 in the present invention. When the pH is higher than 8, undesirable side reactions occur to reduce the yield of the isocyanate compound of the general formula II. On the contrary, when the pH is lower than 4, the reactions of the alkoxysilyl group and the like are accelerated to form polymers such as polysiloxanes in the reaction system to reduce the yield of the isocyanate compound. Thus, for obtaining a high yield of the highly pure silicon-containing isocyanate compound, it is important to control the pH of the reaction system not higher than 8 in the present invention. The pH is controlled preferably with a mineral acid such as hydrochloric, sulfuric, nitric or phosphoric acid.

The process of the present invention can be conducted by the simultaneous distillation with the thermally induced decomposition, wherein the urethane compound is decomposed in the presence of the metallic catalyst preferably in an inert solvent at pH 8 or below and then the resultant isocyanate compound of the general formula II and alcohol are partially condensed outside the reaction system. The carbamic ester can be thermally decomposed at a temperature of 350° C. or below, preferably 80° to 350° C. and still preferably 80° to 300° C. When the temperature is below 80° C., the practical reaction rate cannot be obtained and, on the contrary, when it is as high as above 350° C., undesirable side reactions such as the polymerization of the isocyanate occur. The reaction pressure is such that under which the formed isocyanate compound of the general formula II and alcohol can be gasified at the reaction temperature, such as in the range of 1–500 mm Hg.

The present invention can be conducted either by a batch reaction method wherein the carbamic ester, inert solvent and decomposition catalyst are fed at once or, by a continuous reaction method wherein the carbamic ester is continuously fed into the inert solvent containing the decomposition catalyst under reduced pressure.

EXAMPLE 1

A 300 ml three-necked flask provided with a capillary, a thermometer, a rectifying column and a condenser was used as the reactor. Warm water of 60° C. was passed through the condenser, and the receptor was connected to a vacuum line through a cold trap cooled with ethanol. 100 g of ethyl N-(γ-triethoxysilylpropyl) carbamate, 50 g of ThermS-1000-S (a product of Nippon Steel Chemical Co., Ltd.) as the inert solvent and 0.075 g of dibutyltin dilaurate as the catalyst were fed into the flask and the pH of the resultant mixture was adjusted to 6. The flask was set in an oil bath. After purging the gas from the reaction system with nitrogen, the pressure was reduced to 20 mm Hg, the temperature of the oil bath was elevated to 250° C. and the reaction was continued for 1 h. After the completion of the reaction, the reaction liquid collected in the receptor was determined by gas chromatography to find that γ-triethoxysilylpropyl isocyanate was obtained in a yield of 91.5%.

EXAMPLE 2

100 g of ethyl N-(γ-triethoxysilylpropyl) carbamate, 50 g of ThermS-1000-S (a product of Nippon Steel Chemical Co., Ltd.) as the inert solvent and 0.075 g of iron acetylacetonate as the catalyst were fed into the same reactor as that used in Example 1 and the pH of the resultant mixture was adjusted to 6. The pressure in the reactor was reduced to 20 mm Hg, the temperature of the oil bath was elevated to 250° C. and the reaction was continued for 1 h. After the completion of the reaction, the reaction liquid collected in the receptor was determined by gas chromatography to find that γ-triethoxysilylpropyl isocyanate was obtained in a yield of 90.8%.

EXAMPLE 3

100 g of methyl N-[γ-tris(trimethylsiloxy)silylpropyl] carbamate, 50 g of ThermS-1000-S (a product of Nippon Steel Chemical Co., Ltd.) as the inert solvent and 0.075 g of dibutyltin dilaurate as the catalyst were fed into the same reactor as that used in Example 1 and the pH of the resultant mixture was adjusted to 6. The pressure in the reactor was reduced to 20 mm Hg, the temperature of the oil bath was elevated to 250° C. and the reaction was continued for 1 h. After the completion of the reaction, the reaction liquid collected in the receptor was determined by gas chromatography to find that γ-tris(trimethylsiloxy)silylpropyl isocyanate was obtained in a yield of 92.2%.

Comparative Example 1

100 g of ethyl N-(γ-triethoxysilylpropyl) carbamate, 50 g of ThermS-1000S (a product of Nippon Steel Chemical Co., Ltd.) as the inert solvent and 0.075 g of dibutyltin dilaurate as the catalyst were fed into the same reactor as that used in Example 1. After the completion of the reaction carried out at pH 10, the reaction liquid collected in the receptor was determined by gas chromatography to find that γ-triethoxysilylpropyl isocyanate was obtained in a yield of 70.1%. A large amount of a polymer was formed in the flask.

Comparative Example 2

The thermally induced decomposition reaction was carried out in the same manner as that of Example 1 except that dibutyltin dilaurate as the catalyst was not used. The reaction time was as long as 3 h. After the completion of the reaction, the reaction liquid collected in the receptor was determined by gas chromatography to find that γ-triethoxysilylpropyl isocyanate was obtained in a yield of 70.8%. However, a large amount of a polymer was formed in the flask, since the reaction time was long.

The process of the present invention is superior to the current phosgenation process from the industrial point of view, since the former is free from the problems of handling of highly toxic phosgene, and of the side reaction of HCl, which is formed as a by-product in the process and easily corrode the apparatus.

What is claimed is:

1. A process for producing a silicon-containing isocyanate compound of the general formula II:

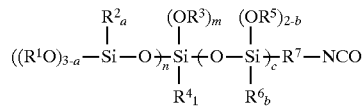

wherein $R^1$ to $R^6$ each represent a hydrocarbon group, $R^7$ represents an alkylene group having 1 to 8 carbon atoms, n, m and l represent an integer of 0 to 3 and m+n+l=3, a represents an integer of 0 to 3, b represents an integer of 0 to 2, and c represents an integer of 0 to 8, said process comprising:

thermally inducing the decomposition of a silicon-containing carbamic ester of the general formula I:

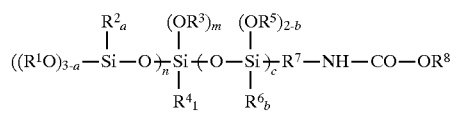

wherein $R^1$ to $R^7$, n, m, l, a, b and c are as defined above, and $R^8$ represents a hydrocarbon group, at a pH of not higher than 8 and at a temperature of not above 350° C. in the presence of a decomposition catalyst comprising at least one metal element selected from the group consisting of Sn, Sb, Fe, Co, Ni, Cu, Cr, Ti and Pb or at least one metal compound thereof, and in an inert solvent having a boiling point higher than that of the isocyanate compound in a weight proportion in the range of 0 to 100 parts per part of the starting carbamic ester of the general formula I, and recovering the isocyanate compound of the general formula II.

2. The process for producing a silicon-containing isocyanate compound according to claim 1, wherein the compounds of the general formulae I and II contain at least one alkoxysilyl group.

3. The process for producing a silicon-containing isocyanate compound according to claim 1, wherein the thermally induced decomposition reaction is carried out at the temperature of 80° to 350° C. under 1 to 500 mm Hg.

4. The process for producing a silicon-containing isocyanate compound according to claim 3, wherein the thermally induced decomposition reaction is carried out at the pH of 4 to 8 and at the temperature of 80° to 300° C.

5. The process for producing a silicon-containing isocyanate compound according to claim 3, further comprising recovering separately an alcohol and the isocyanate compound of the general formula II.

* * * * *